US00PP21528P2

(12) United States Plant Patent
Oudshoorn

(10) Patent No.: US PP21,528 P2
(45) Date of Patent: Nov. 23, 2010

(54) ***SEDUM* PLANT NAMED 'YELLOW XENOX'**

(50) Latin Name: *Hylotelephium spectabile*
Varietal Denomination: Yellow Xenox

(75) Inventor: Hubertus Gerardus Oudshoorn, Rijpwetering (NL)

(73) Assignee: Future Plants Licentie B.V., Lisserbroek (NL)

( * ) Notice: Subject to any disclaimer, the term of this patent is extended or adjusted under 35 U.S.C. 154(b) by 0 days.

(21) Appl. No.: 12/459,832

(22) Filed: Jul. 8, 2009

(51) Int. Cl.
*A01H 5/00* (2006.01)

(52) U.S. Cl. ..... Plt./479

(58) Field of Classification Search ..... Plt./479
See application file for complete search history.

*Primary Examiner*—June Hwu
(74) *Attorney, Agent, or Firm*—C. A. Whealy

(57) ABSTRACT

A new and distinct cultivar of *Sedum* plant named 'Yellow Xenox', characterized by its upright and compact plant habit; basally branching habit; dense and bushy growth habit; attractive light yellow green-colored flowers; and good garden performance.

2 Drawing Sheets

Botanical designation: *Hylotelephium spectabile.*
Cultivar denomination: 'Yellow Xenox'.

BACKGROUND OF THE INVENTION

The present invention relates to a new and distinct cultivar of *Sedum* plant, botanically known as *Hylotelephium spectabile* and hereinafter referred to by the name 'Yellow Xenox'.

The new *Sedum* plant is a product of a planned breeding program conducted by the Inventor in Rijpwetering, The Netherlands. The objective of the breeding program is to create new strong and healthy *Sedum* cultivars with numerous attractive flowers.

The new *Sedum* plant originated from a cross-pollination during the summer of 2005 in Rijpwetering, The Netherlands, of *Sedum telephium* 'Xenox', disclosed in U.S. Plant Pat. No. 16,888, as the female, or seed, parent with *Sedum telephium* 'Sunkissed', disclosed in U.S. Plant Pat. No. 16,927, as the male, or pollen, parent. The new *Sedum* was discovered and selected by the Inventor as a single flowering plant within the progeny of the stated cross-pollination in a controlled greenhouse environment in Rijpwetering, The Netherlands during the summer of 2006.

Asexual reproduction of the new *Sedum* plant by vegetative cuttings in a controlled environment in Rijpwetering, The Netherlands since the summer of 2006, has shown that the unique features of this new *Sedum* plant are stable and reproduced true to type in successive generations.

SUMMARY OF THE INVENTION

Plants of the new *Sedum* have not been observed under all possible environmental conditions. The phenotype may vary somewhat with variations in environment such as temperature and light intensity without, however, any variance in genotype.

The following traits have been repeatedly observed and are determined to be the unique characteristics of 'Yellow Xenox'. These characteristics in combination distinguish 'Yellow Xenox' as a new and distinct cultivar of *Sedum:*

1. Upright and compact plant habit.
2. Basally branching habit; dense and bushy growth habit.

3. Attractive light yellow green-colored flower.
4. Good garden performance.

Plants of the new *Sedum* differ from plants of the female parent, 'Xenox', primarily in flower color as plants of 'Xenox' have orange white to greyed yellow-colored flowers.

Plants of the new *Sedum* differ from plants of the male parent, 'Sunkissed' primarily in leaf color as plants of 'Sunkissed' have green to yellow green-colored leaves.

Plants of the new *Sedum* can be compared to plants of *Sedum telephium* 'Bronco', disclosed in U.S. Plant Pat. No. 18,085. Plants of the new *Sedum* and 'Bronco' differ in the following characteristics:

1. Plants of the new *Sedum* are more compact than plants of 'Bronco'.
2. Plants of the new *Sedum* and 'Bronco' differ in leaf coloration.

BRIEF DESCRIPTION OF THE PHOTOGRAPHS

The accompanying colored photographs illustrate the overall appearance of the new *Sedum* plant, showing the colors as true as it is reasonably possible to obtain in colored reproductions of this type. Colors in the photographs may differ slightly from the color values cited in the detailed botanical description which accurately describe the colors of the new *Sedum* plant.

The photograph on the first sheet comprises a side perspective view of a typical flowering plant of 'Yellow Xenox' grown in a container.

The photograph at the top of the second sheet is a close-up view of typical inflorescences of 'Yellow Xenox'.

The photograph at the bottom of the second sheet is a close-up view of a typical leaf of 'Yellow Xenox'.

DETAILED BOTANICAL DESCRIPTION

The aforementioned photographs and following observations, measurements and values describe plants grown in Rijpwetering, The Netherlands, under commercial practice during the late summer in an outdoor nursery with day temperatures ranging from 12° C. to 32° C. and night temperatures ranging from 6° C. to 18° C. Plants used in the photographs and description were two years old. In the following description, color references are made to The Royal Horticultural Society Colour Chart, 2007 Edition, except where general terms of ordinary dictionary significance are used.

Botanical classification: *Hylotelephium spectabile* 'Yellow Xenox'.

Parentage:

*Female, or seed, parent.*—*Sedum telephium* 'Xenox', disclosed in U.S. Plant Pat. No. 16,888.

*Male, or pollen, parent.*—*Sedum telephium* 'Sunkissed', disclosed in U.S. Plant Pat. No. 16,927.

Propagation:

*Type.*—By vegetative cuttings.

*Time to initiate roots.*—About 15 to 20 days at 18° C.

*Time to produce a rooted young plant.*—About two months at 16° C. to 22° C.

*Root description.*—Moderately thick and moderately fleshy; white to medium brown in color.

*Rooting habit.*—Moderately freely branching; moderately dense.

Plant description:

*Plant form/habit.*—Herbaceous perennial; upright and compact plant habit; broad inverted triangle; moderately vigorous growth habit; freely basally branching habit with about four basal branches developing per plant; dense and bushy growth habit.

*Plant height.*—About 19.8 cm.

*Plant width* (*spread*).—About 19.8 cm.

*Lateral branches.*—Length: About 9.8 cm. Diameter: About 5 mm. Internode length: About 4.8 cm. Strength: Strong. Texture: Smooth, glabrous. Color: Close to 187A; at the nodes, close to 146C.

Foliage description:

*Arrangement.*—Opposite, simple; sessile.

*Length.*—About 7.3 cm.

*Width.*—About 5.4 cm.

*Shape.*—Ovate.

*Apex.*—Bluntly acute to rounded.

*Base.*—Truncate.

*Margin.*—Irregularly and shallowly dentate.

*Texture, upper and lower surfaces.*—Smooth, glabrous; succulent.

*Venation pattern.*—Pinnate.

*Color.*—Developing leaves, upper surface: Between 137A and 147A. Developing leaves, lower surface: Close to 147B. Fully expanded leaves, upper surface: Between 147A and darker than N189A; strongly tinged with close to N186C; venation, close to N186C. Fully expanded leaves, lower surface: Close to 191A; venation, close to N186C.

Flower description:

*Flower type/habit.*—Small rotate flowers arranged in terminal compound cymes; flowers face upright to slightly outward; freely flowering habit with about 1,600 flower buds and flowers developing per plant.

*Fragrance.*—None detected.

*Natural flowering season.*—Continuously flowering during August and September in The Netherlands.

*Postproduction longevity.*—Flowers last about two weeks on the plant; flowers persistent.

*Flower buds.*—Height: About 5 mm. Diameter: About 3 mm. Shape: Ovate. Color: Close to 144A, strongly tinged with close to 183A.

*Inflorescence height.*—About 8.4 cm.

*Inflorescence diameter.*—About 8.3 cm.

*Flower diameter.*—About 7 mm.

*Flower depth.*—About 6 mm.

*Petals.*—Quantity per flower: Typically five in a single whorl; petals fused at the base. Length: About 6 mm. Lobe width: About 2 mm. Shape: Ovate. Apex: Acute. Margin: Entire. Texture, upper and lower surfaces: Smooth, glabrous. Color: When opening and fully opened, upper surface: Close to 145D; towards the apex, close to 146A to 146B. When opening and fully opened, lower surface: Close to 146C to 146D; towards the apex, close to 146A to 146B.

*Sepals.*—Quantity per flower: Typically five in a single whorl, fused at the base. Length: About 2 mm. Width: About 1 mm. Shape: Narrowly ovate. Apex: Acute. Margin: Entire. Texture, upper and lower surfaces: Smooth, glabrous. Color: When opening, upper and lower surfaces: Close to 146B. Fully opened, upper and lower surfaces: Close to 146B.

*Peduncles.*—Length: About 6.1 cm. Diameter: About 3 mm. Angle: Erect to about 30° from vertical. Strength: Moderately strong. Texture: Smooth, glabrous. Color: Close to 187A.

*Pedicels.*—Length: About 4 mm. Diameter: About 0.7 mm. Angle: Erect to about 40° from vertical. Strength: Moderately strong. Texture: Smooth, glabrous. Color: Close to 200C flushed with close to 187A.

*Reproductive organs.*—Stamens: Quantity per flower: Typically ten. Filament length: About 4 mm. Filament color: Close to 4D. Anther shape: Broadly oblong, flattened. Anther length: About 0.7 mm. Anther color: Close to 42B. Pollen amount: Scarce. Pollen color: Close to 12B. Pistils: Quantity per flower: Five. Pistil length: About 4.5 mm. Stigma shape: Pointed. Stigma color: Close to 22A. Style length: About 4 mm. Style color: Close to 1A. Ovary color: Close to 1A.

*Seed/fruit.*—Seed and fruit development have not been observed.

Disease/pest resistance: Plants of the new *Sedum* have not been noted to be resistant to pathogens and pests common to *Sedum*.

Garden performance: Plants of the new *Sedum* have been observed to have good garden performance and tolerate rain and wind. Plants of the new *Sedum* tolerate high temperatures of about 35° C. and are winter hardy to USDA Hardiness Zone 5.

It is claimed:

1. A new and distinct *Sedum* plant named 'Yellow Xenox' as illustrated and described.

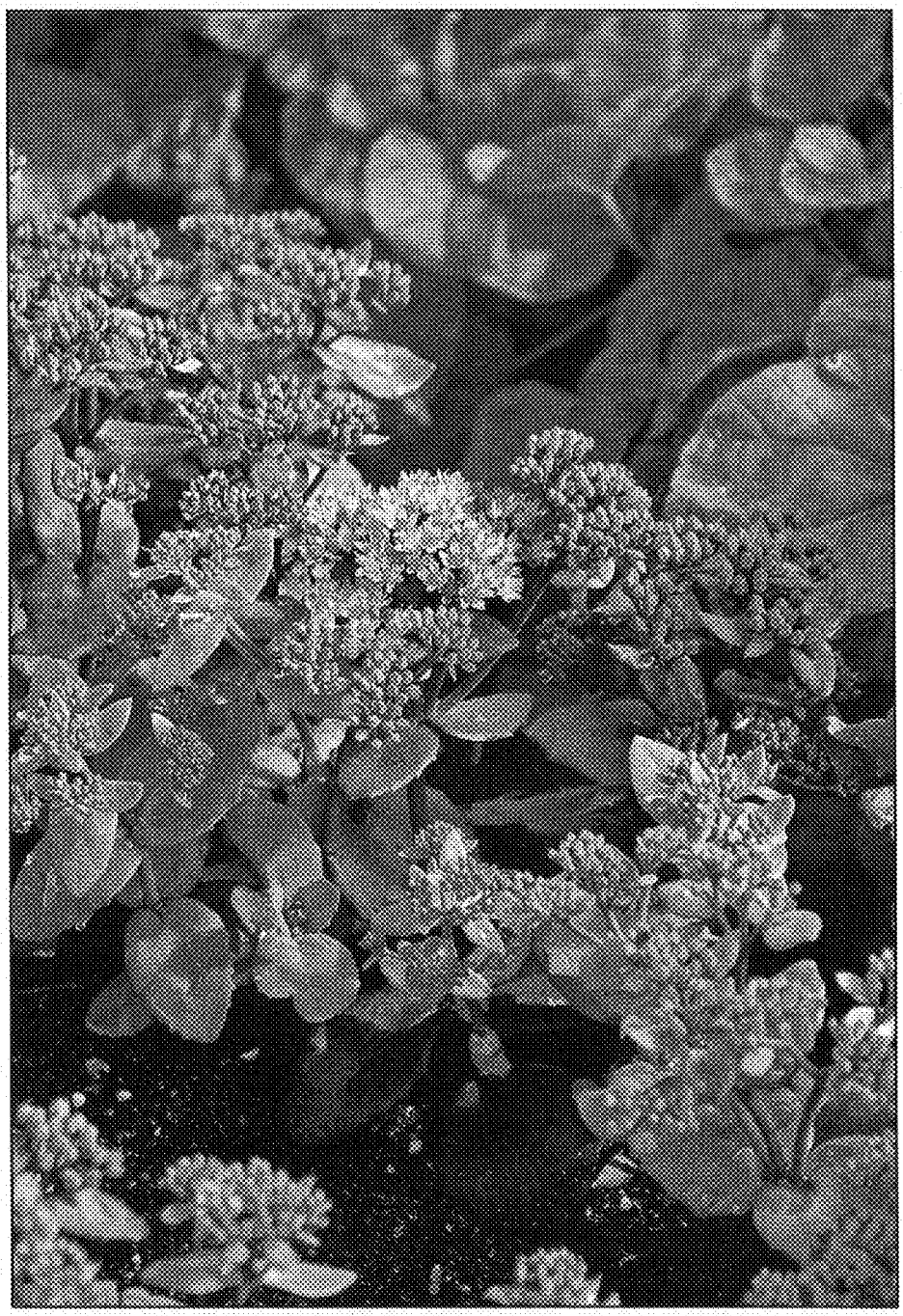

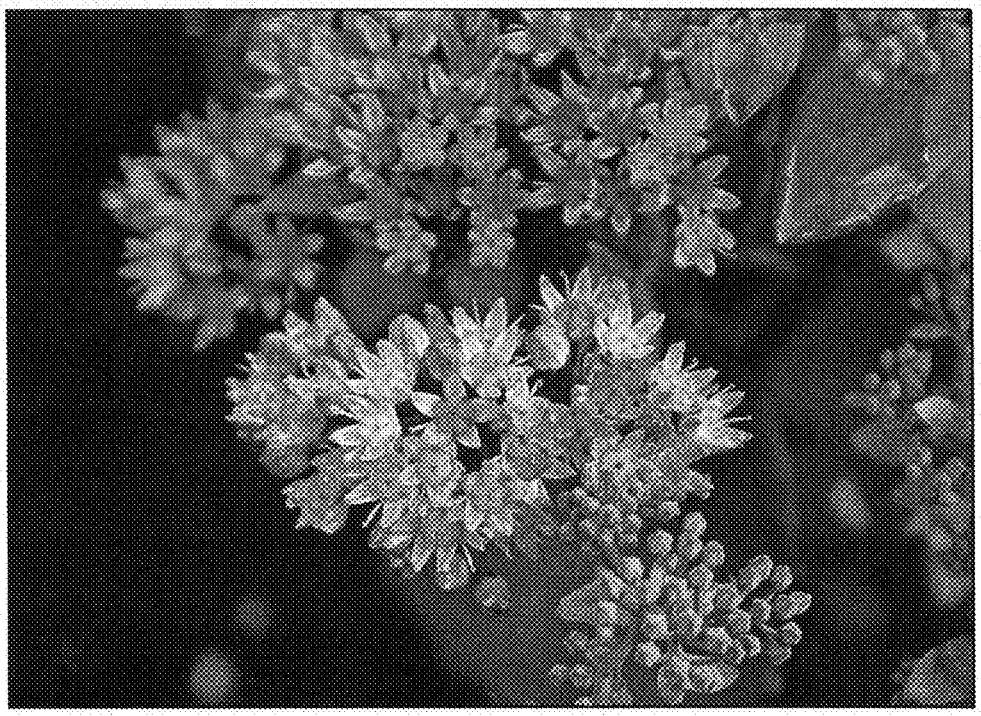
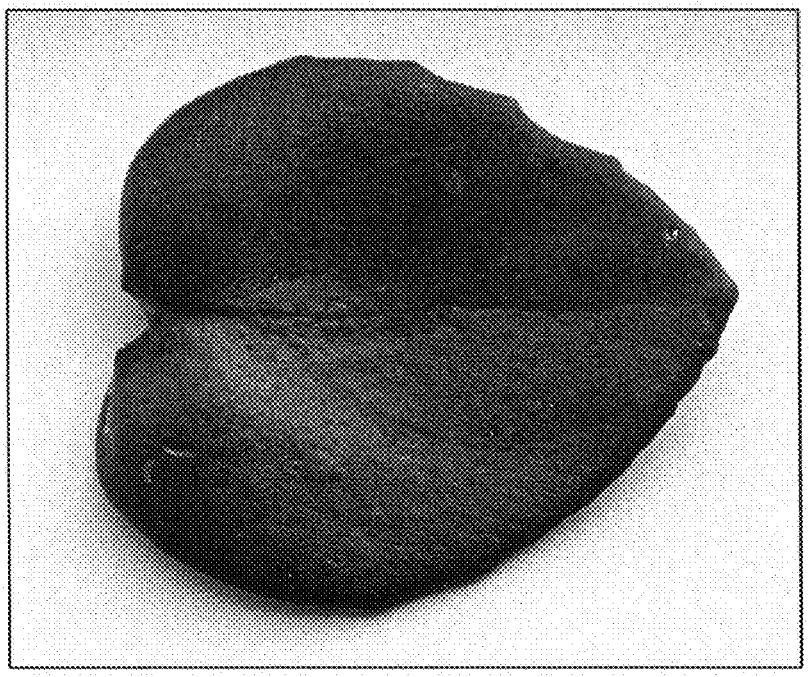

* * * * *